(12) United States Patent
Karim et al.

(10) Patent No.: US 8,575,355 B2
(45) Date of Patent: Nov. 5, 2013

(54) DI-THIAZOLYL-BENZODIAZOLE BASED SENSITIZERS AND THEIR USE IN PHOTOVOLTAIC CELL

(75) Inventors: Mohammad Rezaul Karim, Riyadh (SA); Md. Akhtaruzzaman, Riyadh (SA); Ashraful Islam, Riyadh (SA); Abdulrahman M. Al-Ahmari, Riyadh (SA)

(73) Assignee: King Abdulaziz City for Science and Technology, Riyadh (SA)

( * ) Notice: Subject to any disclaimer, the term of this patent is extended or adjusted under 35 U.S.C. 154(b) by 0 days.

(21) Appl. No.: 13/336,536

(22) Filed: Dec. 23, 2011

(65) Prior Publication Data

US 2013/0160854 A1    Jun. 27, 2013

(51) Int. Cl.
*C07D 417/14*   (2006.01)

(52) U.S. Cl.
USPC ............................................ 548/134

(58) Field of Classification Search
USPC ............................................ 548/134
See application file for complete search history.

(56) References Cited

PUBLICATIONS

Akhtaruzzaman et al. Chem. Commun. 2005, 3183-3185.*
Weihong Zhu "Organic D-A-π-A Solar Cell Sensitizers with Improved Stability and Spectral Response", Advanced Functional Materials, 2011, pp. 756-763, 21, Shanghai, China.
Md. Akhtaruzzaman "Synthesis, characterization and FET properties of novel dithiazolylbenzothiadiazole derivatives", Chemical Commun, 2005, pp. 3183-3185.
Masaki Matsui "The use of indoline dyes in a zinc oxide dye-sensitized solar cell", Elsevier, Dyes and Pigments 80, 2009, pp. 233-238.
Okiko Miyata "Efficient synthesis of indoles using [3,3]-sigmatropic rearrangement of N-trifluoroacetyl enehydrazines", Elsevier, Tetrahedron 62, 2006, pp. 3629-3647.
Shinji Higashijima Highly efficent new indoline dye having strong electron-withdrawing group for zinc . . . cell, Elsevier, Tetrahedron 67, 2011, pp. 6289-6293.
David Cousin "A new approach to combretastatin D2", Org. Biomol. Chem., 2006, 4, pp. 54-62.

* cited by examiner

*Primary Examiner* — Joseph Kosack
*Assistant Examiner* — Matthew Coughlin
(74) *Attorney, Agent, or Firm* — Andrew M. Calderon; Roberts Mlotkowski Safran & Cole, P.C.

(57) ABSTRACT

Described herein are D-π-A type sensitizers of the formula (I) or (II)

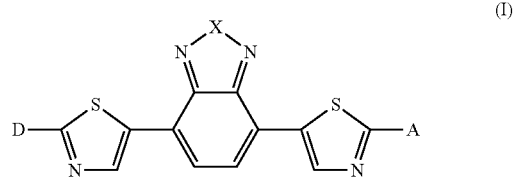

(I)

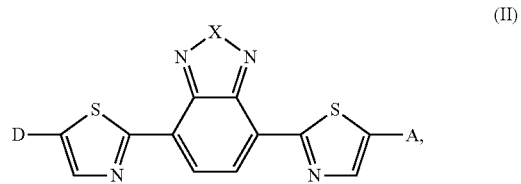

(II)

having a novel central π-conjugated unit di-thiazolyl-benzodiazole and dye-sensitized electrodes including a substrate having an electrically conductive surface, an oxide semiconductor film formed on the conductive surface, and the above sensitizer of formula (I) or (II), as specified above, supported on the film. A solar cell includes the above electrode, a counter electrode, and an electrolyte deposited there between. The sensitizers of formula (I) and (II) efficiently sensitize the semiconductor materials and show a high solar to electricity conversion efficiency.

7 Claims, 1 Drawing Sheet

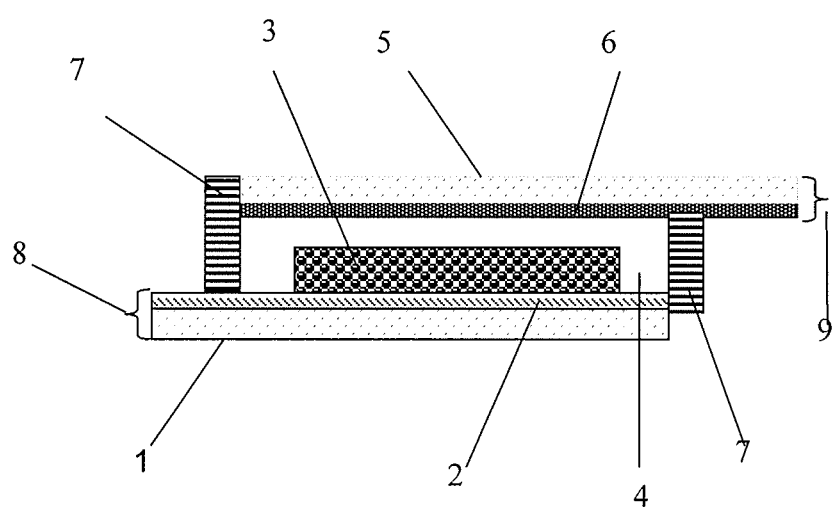

DI-THIAZOLYL-BENZODIAZOLE BASED SENSITIZERS AND THEIR USE IN PHOTOVOLTAIC CELL

FIELD

This invention relates to di-thiazolyl-benzodiazole based sensitizers and their use in photovoltaic cell, such as solar cells.

BACKGROUND

Photosensitive dyes are coated on metal oxide films to render devices, such as solar cells, effective in the conversion of visible light to electric energy. In such a solar cell, a monolayer of dye is attached to the surface of a nanocrystalline metal dioxide film. Most efficient organic sensitizers contain a donor and an acceptor bridged by a π-conjugation linker (D-π-A). A great variety of organic sensitizers based on coumarin, merocyanine, indoline, polyene, hemicyanine, triphenylamine, fluorene tetrahydroquinoline, porphyrin, and carbazole moieties as a donor group give respectable conversion efficiencies in dye-sensitized solar cells. Most of the D-π-A dyes have carboxylic acid, cyanoacrylic acid or rhodanine-3-acetic acid moieties as electron acceptors, and also as anchoring groups for attachment on $TiO_2$ surfaces. Carboxy groups can form ester linkages with $TiO_2$ surfaces to provide strongly bound dyes and good electron communication. The photoabsorption properties of a D-π-A dye are associated with intramolecular charge transfer (ICT) excitation from the donor to the acceptor moiety of the dye, resulting in efficient electron transfer through the acceptor moiety (carboxy group) from the excited dye into the $TiO_2$ conduction band. The charge transfer or separation between the electron donor and acceptor moieties in the excited dye may facilitate rapid electron injection from the dye molecule into the conduction band of the $TiO_2$, so that it would be expected to separate the cationic charge effectively from the $TiO_2$ surface and to restrict recombination between the injected electron and the oxidized dye efficiently.

As a noteworthy structural feature of D-π-A dyes, the highest occupied molecular orbitals (HOMOs) are in many cases delocalized over the n-conjugated systems in configurations centering on donor parts, while the lowest unoccupied molecular orbitals (LUMOs) are delocalized over acceptor and anchor parts. The photoinduced electron transfer from D-π-A dyes to $TiO_2$ electrodes can thus efficiently occur by ICT with respect to HOMO-to-LUMO transition. Photoexcitation of the dye results in the injection of an electron into the conduction band of the metal oxide. The original state of the dye is subsequently restored by electron donation from a redox system, such as iodide/triiodide couple. Molecular design of new photosensitizers for nanocrystalline $TiO_2$ film in solar cell that can absorb visible lights of all colors presents a challenging task. The absorption spectra of organic dyes could be red-shifted by expansion of the it conjugation in the dyes and introduction of electron-donating and—accepting substituents into the dye skeletons. The dyes should have suitable ground- and excited state redox properties so that the charge injection and regeneration of the dye occur efficiently.

As relevant art is mentioned in Adv. Funct. Mater. 2011, 21, 756-763.

SUMMARY

The present invention aims to provide a new series of di-thiazolyl-benzodiazole based D-π-A sensitizers for use in dye sensitized nanocrystalline solar cells.

According to the invention, there is provided photosensitive dye represented by the formula I or the formula II:

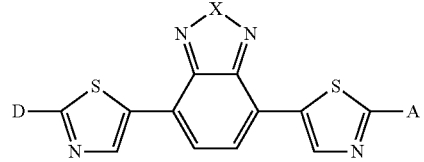

(I)

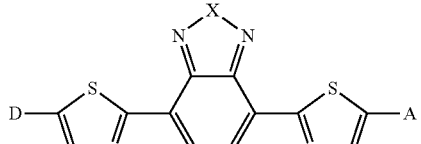

(II)

wherein X is selected from S, Se and $CH_2$;

D is a donor group selected from D-1 and D-2:

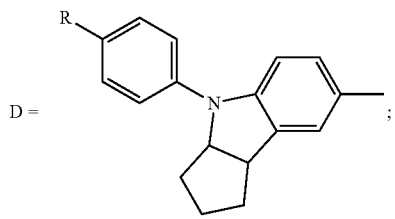

$R = \!\!-\!\!-\!\!C_nH_{2n+1}$  D-1a $R = \!\!-\!\!-\!\!O\!\!-\!\!C_nH_{2n+1}$  D-1b

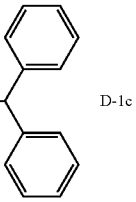

R =  D-1c

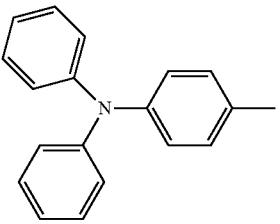

D-2 where n=1 to 12 (alkyl group having 1 to 12 carbon atoms): and

A is an acceptor having one anchoring group selected from A-(1-4):

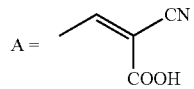

A-1

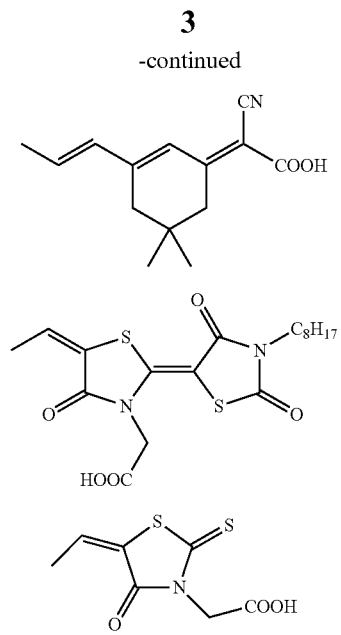

A-2

A-3

A-4

The present invention further provides a photovoltaic cell comprising a support, a conductive layer formed on the support, and a porous semiconductor layer formed on the conductive layer, wherein the porous semiconductor layer carries a photosensitizing dye as defined above.

These and other advantages of the present invention will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention is described in the detailed description which follows, in reference to the noted drawing by way of non-limiting examples of exemplary embodiments of the present invention.

The FIGURE is a diagrammatic sectional view showing the structure of a solar cell constructed in accordance with one example the present invention.

DETAILED DESCRIPTION OF THE EMBODIMENTS

Described herein is a novel photosensitive dye and its use in a photovoltaic cell, such as a solar cell. The novel photosensitive dye comprises a compound represented by the formula I or the formula II:

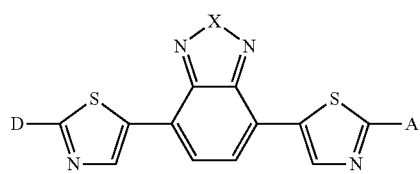

(I)

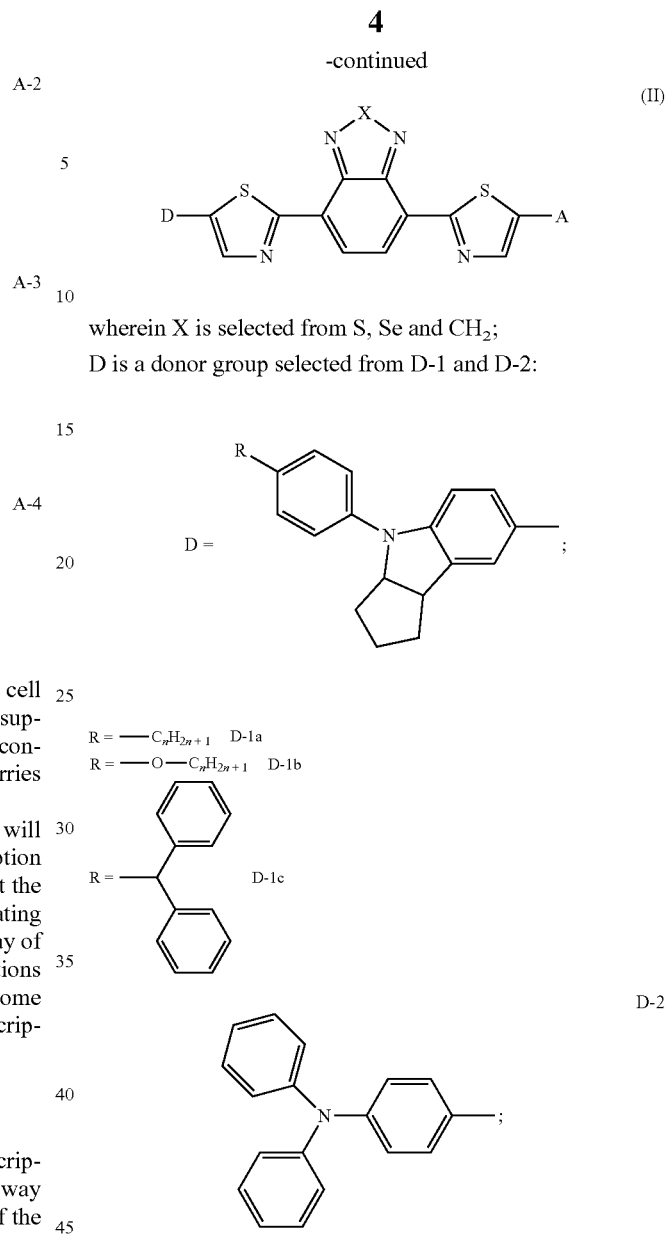

(II)

wherein X is selected from S, Se and $CH_2$;

D is a donor group selected from D-1 and D-2:

where n=1 to 12 (alkyl group having 1 to 12 carbon atoms): and

A is an acceptor having one anchoring group selected from A-(1-4):

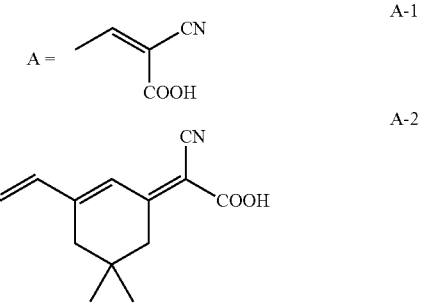

A-1

A-2

-continued
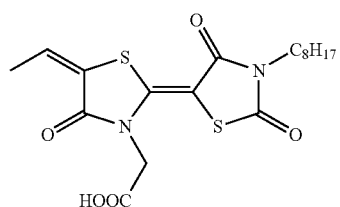
A-3
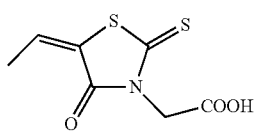
A-4
Specifically, preferred illustrative examples of the photosensitizing organic dyes of the general formula (II) are C-1 to C-7.
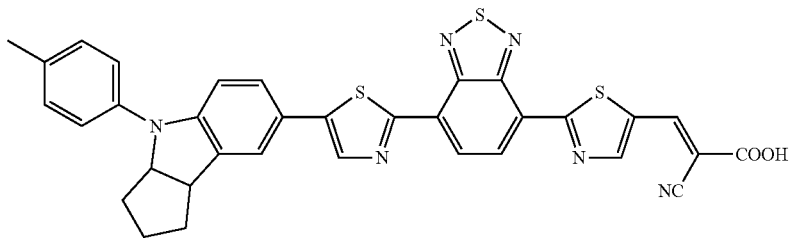
C-1
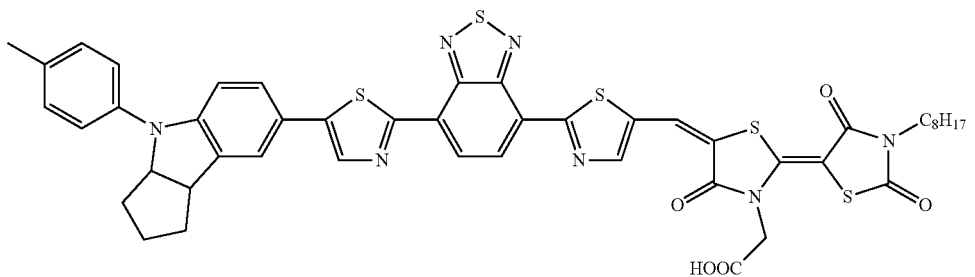
C-2
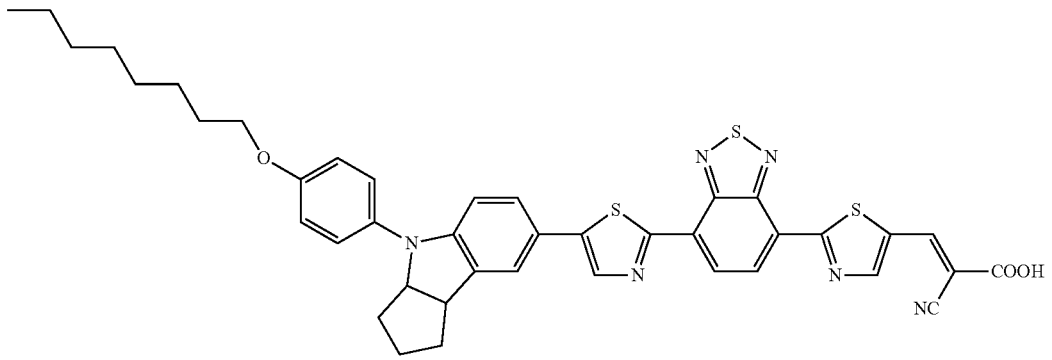
C-3
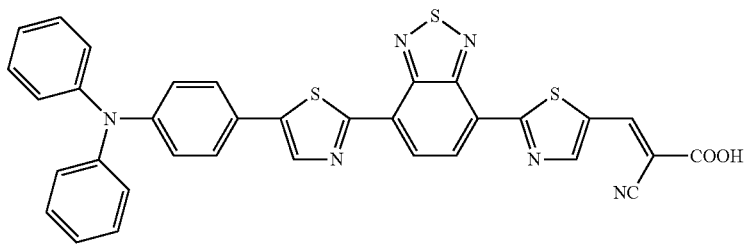
C-4

-continued

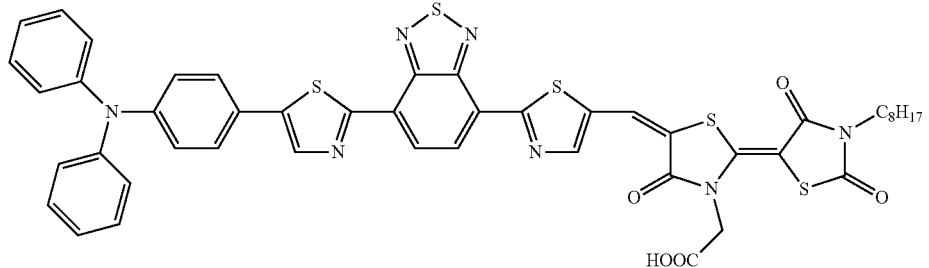

C-5

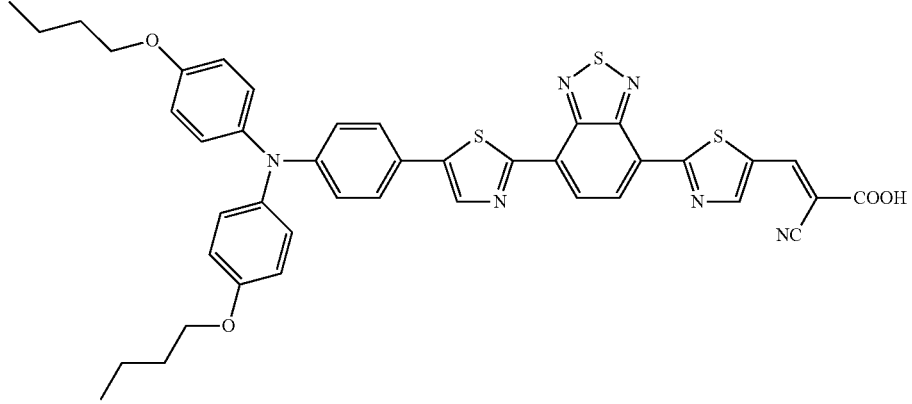

C-6

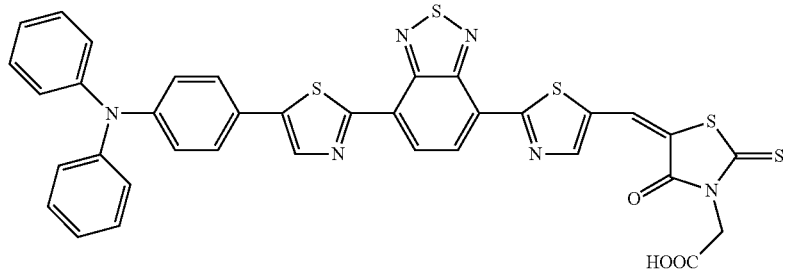

C-7

An embodiment of the present invention will be described with reference to the FIGURE. A dye-sensitized solar cell shown in FIG. 1 comprises an electroconductive support 8, a porous photovoltaic layer 3 having a photosensitizing dye adsorbed thereon and/or therein formed on the electroconductive support 8, a counter electrode 9, a hole transporting layer 4 mounted between the porous photovoltaic layer 3 and the counter electrode side 9, and a sealant 7 sealing the side surfaces of the device.

The electroconductive support 8 is composed of a substrate 1 and a transparent electroconductive film 2. The material used in the substrate 1 is not particularly limited and can be various kinds of transparent materials, with glass being preferred. The material used in the transparent electroconductive film 2 is also not particularly limited, and it is preferred to use a transparent electroconductive metallic oxide electrode such as fluorine-doped tin oxide ($SnO_2$:F). The material of the porous semiconductor layer used in the porous photovoltaic layer 3 is preferably an oxide semiconductor such as titanium oxide ($TiO_2$), zinc oxide (ZnO) and tin oxide ($SnO_2$). The oxide semiconductor preferably has a particle diameter of 6 to 100 nm, more preferably 30 nm or less. The oxide semiconductor is immobilized on the conductive surface to form a generally porous film having a thickness of at least 500 nm, preferably 5000 to 15000 nm.

A dye sensitized semiconductor electrode may be obtained by depositing the above described organic sensitizers on a film or layer of oxide semiconductor particles formed on an electrically conductive surface of a substrate in any suitable conventional manner.

Formation of the oxide semiconductor on the conductive surface may be effected by coating the surface with a suspension or slurry containing the oxide semiconductor, followed by drying and calcination. The calcination is generally carried out at 300 to 700° C., preferably 400 to 500° C.

The organic sensitizer is deposited on the semiconductor layer. This is conveniently achieved by dissolving the organic sensitizer in a suitable solvent, such as methanol, ethanol, acetonitrile, tert-butanol or dimethylformamide. The above described semiconductor electrode is then impregnated with this solution by immersion, coating or any other suitable method. It is preferred that the solution penetrates deep into the porous layer of the oxide semiconductor. The organic sensitizers preferably form a monolayer on surfaces of the oxide semiconductor.

The counter electrode 9 comprises a substrate 5 and a counter electrode layer 6. The material used for the substrate 5 can be various kinds of transparent materials, with glass being preferably used. The material used for the counter electrode layer 6 is also not particularly limited, and one of a platinum thin film, a carbon thin film, fluorine-doped tin oxide (SnO$_2$:F), tin-doped indium oxide (In$_2$O$_3$:Sn), and a composite film of plurality thereof can be used. The role of the counter electrode layer 6 is to facilitate the transfer of electrons from the counter electrode to the electrolyte. Further the outside of the substrates may be coated with plastics like PS, PMMA, or preferably PC to protect the TiO2 layer, the dye-stuff and the electrolyte against UV-light to give long term stability.

As the hole transporting layer 4 any material that can transport an electron, a hole or an ion can be used. For example, a hole transporting material such as polyvinyl carbazole, an electron transporting material such as tetranitrofluorenone, an electroconductive polymer such as polypyrrol, a liquid electrolyte, and an ionic electroconductive material such as a polymer solid electrolyte, can be used.

Illustrative of the redox pairs for a liquid electrolyte are I$^-$/I$_3^-$, Br$^-$/Br$_3^-$ and quinone/ hydroquinone pairs. In the case of I$^-$/I$_3^-$, for example, lithium iodide and iodine may be used. Acetonitrile or propylene carbonate can be used as an electrochemically inert solvent capable of dissolving the electrolyte in a large amount.

The following non-limiting Examples will further illustrate the present invention.

EXAMPLE 1

Synthesis Process for Dye C-1

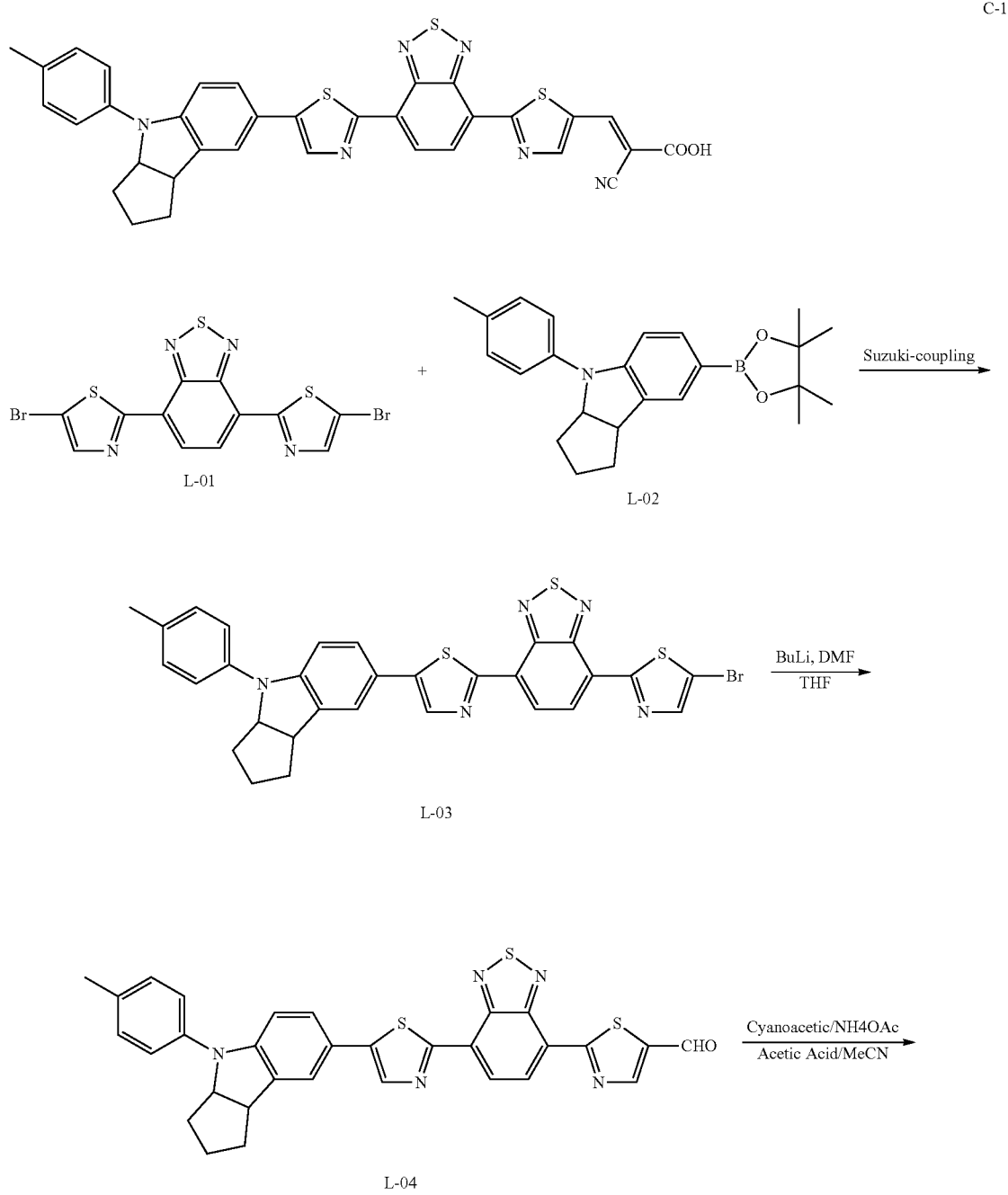

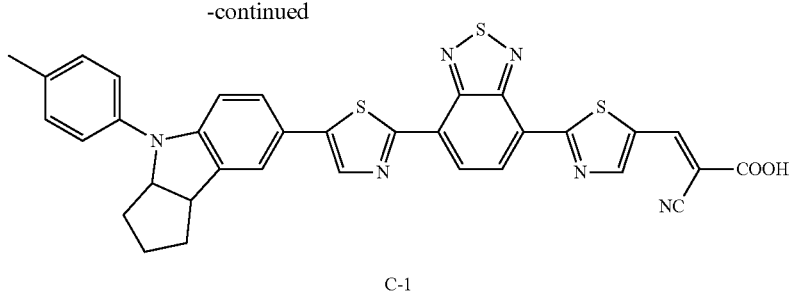

C-1

Preparation of Compound L-01:

Compound L-01 was prepared by an analogous procedure to that described in Md. Akhtaruzzaman, Naoto Kamata, Jun-ichi Nishida, Shinji Ando, Hirokasu Tada, Masaaki Tomura, Yoshiro Yamashita, *Chem. Commun.*, 2005, 3183, as illustrated below.

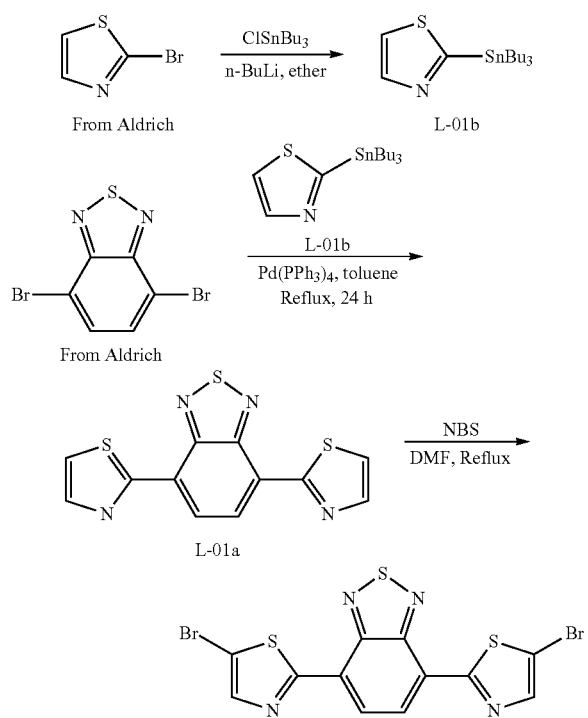

Ref. 1: Md. Akhtaruzzaman et. al., Chem. Commun., 2005, 3183.

Synthesis of L-01b: Under argon a solution of n-BuLi in hexanes (6.14 mmol, 2.5 M) was dropped into a stirred solution of 2-bromothiazole (3.07 mmol) in dry ether at 0° C. After 1 h the mixture was cooled to −78° C. and a solution of tributyltin chloride (3.07 mmol) in dry ether was slowly added and the mixture was stirred overnight. The mixture was then added to water (50 ml). The aqueous layer was extracted with ether (3×30 ml). The combined organic layers were dried with magnesium sulfate, and the solvent was removed in vacuo to give the title product L-01b as a pale brown oil in quantitative yield which was used for synthesis of compound L-01a without further purification.

Synthesis of L-01a: A degassed solution of the 2,1,3-dibromobenzothiadiazole (source: Aldrich) (2.8 mmol), the compound L-01b (3.07 mmol) and Pd(PPh$_3$)$_4$ (0.056 mmol) in toluene (5 ml) was heated at 80° C. under argon. After 24 h the reaction mixture was cooled to room temperature, filtered and washed washed with a saturated solution of KF (3×50 ml), water (3×50 ml) and a saturated solution of NaCl (100 ml). The resulting organic layer was dried with magnesium sulfate, and the solvent was removed in vacuo and recrystallized from n-hexane to give the compound L-01 a as a yellow solid. Anal. C$_{12}$H$_6$N$_4$S$_3$: Calcd: C, 47.66; H, 2.00; N, 18.53; Found: C, 47.72; H, 2.09; N, 18.61. MS (ESIMS): m/z: 301.9.

Synthesis of compound L-01: To a solution of compound L-01a (0.45 mmol) in acetone (4.5 mL) was added N-bromosuccinimide (NBS) (0.50 mmol) at 0° C. under a nitrogen atmosphere in the dark. After being stirred at the same temperature for 2 h, the reaction mixture was quenched with H$_2$O and extracted with CHCl$_3$. The organic phase was washed with brine, dried over MgSO4 and concentrated at reduced pressure. The crude solid obtained was recrystallized from n-hexane to afford compound L-01 (91%) as light yellow solids. Anal. C$_{12}$H$_4$Br$_2$N$_4$S$_3$: Calcd: C, 31.32; H, 0.88; N, 12.17; Found: C, 31.41; H, 0.86; N, 12.22. MS (ESIMS): m/z: 459.7.

Preparation of compound L-02: This compound was prepared by an analogous procedure to that described in the following references: M. Matsui, A. Ito, M. Kotani, Y, Kubota, K, Funabiki, J, Jin, T, Yoshida, H. Minoura, H. Miura., *Dyes and Pigments.*, 80, (2009), 233; O. Miyata, N. Takeda, Y. Kimura, Y. Takemoto, N. Tohnai, M. Miyata, T. Naito, *Tetrahedron* 2006, 62, 3629; D. Cousin, J. Mann, M. Nieuwenhuyzen, H. v. d. Berg, *Org. Biomol. Chem.* 2006, 4, 54, as illustrated below.

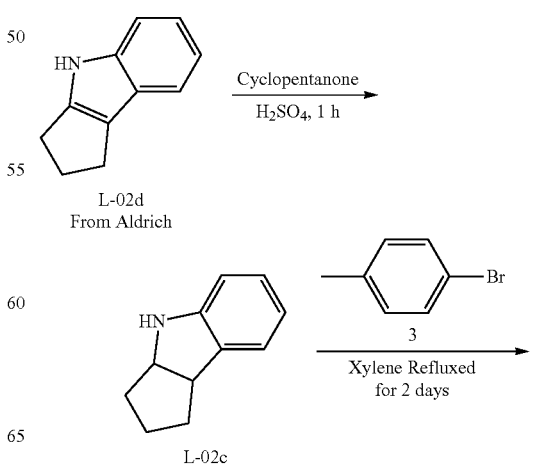

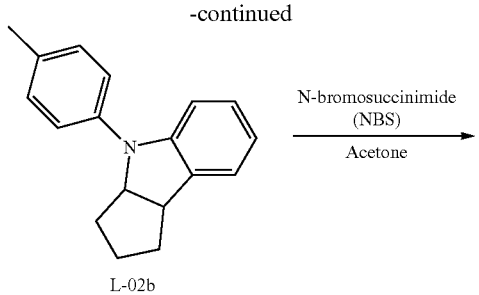

L-02b
Ref. Dye and pig., 2009, 80, 2333.

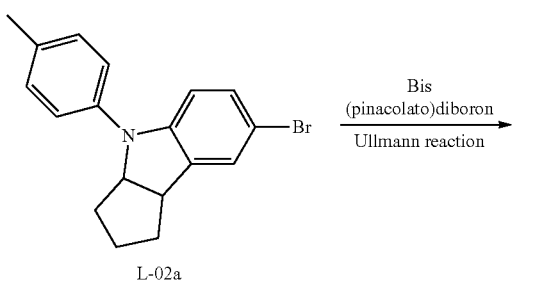

L-02a
Ref. Tetrahedron 2006, 62, 3629

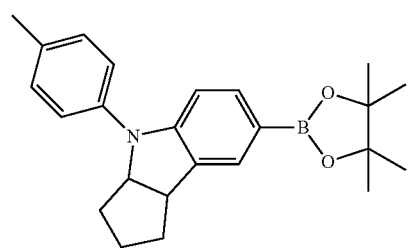

L-02
Ref. Chem. Mater. 2011, 23, 4394

Synthesis of L-02b: To xylene (37 ml) were added 1,2,3,3a,4,8b-hexahydrocyclopenta[b] indole (2), (10 mmol), aromatic bromides 3 (10 mmol), cesium carbonate (14 mmol), palladium acetate (5.4×10-2 mmol), and tri-tertbutylphosphine (1 mmol). The mixture was refluxed for 24 h. After the reaction was completed, the mixture was filtered. The filtrate was washed with a saturated aqueous ammonium chloride (20 ml×3). Compounds L-02b was purified by silica gel column chromatography (toluene). Anal. $C_{18}H_{19}N$: Calcd: C, 86.70; H, 7.68; N, 5.62; Found: C, 86.81; H, 7.65; N, 5.69. MS (ESIMS): m/z: 249.1.

Synthesis of Compounds L-02a: To a solution of compound L-02b (0.45 mmol) in acetone (4.5 mL) was added N-bromosuccinimide (NBS) (0.50 mmol) at 0° C. under a nitrogen atmosphere in the dark. After being stirred at the same temperature for 2 h, the reaction mixture was quenched with $H_2O$ and extracted with $CHCl_3$. The organic phase was washed with brine, dried over MgSO4 and concentrated at reduced pressure. The crude solid obtained was recrystallized from n-hexane to afford the compound L-02a (97%) as light yellow solids. Anal. $C_{18}H_{18}BrN$: Calcd: C, 65.86; H, 5.53; N, 4.27; Found: C, 65.93; H, 5.48; N, 4.33. MS (ESIMS): m/z: 327.0.

Synthesis of compound L-02: In a nitrogen atmosphere, 1.61 mmol of compound L-02a and 3.54 mmol of bis(pinacolato)diboron were dissolved in 50 mL of DMF followed by the addition of 3 mol % of palladium acetate and 4.82 mmol of potassium acetate. The reaction mixture was then stirred at 80° C. while the progress of the reaction was monitored by TLC on silica with toluene as eluent. After 7 h an almost complete consumption of starting material and monoborylated product was indicated. Therefore, the hot reaction mixture was poured into 100 mL of water leading to precipitation of a microcrystalline light yellow product, which was filtered off and dried in the air. The residue was treated with dichloromethane and insoluble material was filtered off. Recrystallization from ethanol afforded the product as a yellow solid. Yield 45%. Anal. $C_{24}H_{30}BNO_2$: Calcd: C, 76.80; H, 8.06; N, 3.73; Found: C, 76.89; H, 8.12; N, 3.81. MS (ESIMS): m/z: 375.2

Preparation of Compound L-03: To a mixture of 4,7-Dibromodithiazolylbenzothiadiazole (L-01) (1.50 mmol), 1,2,3,3a,4,8b- hexahydro-4-(4-methylphenyl)-cyclopent[b]indole boronic ester (L-02) (1.38 mmol), Pd(PPh$_3$)$_4$ (0.078 mmol), $K_2CO_3$ (2.0 mmol) in THF (20 ml) was added 2 ml of $H_2O$ and the mixture was refluxed for 16 h under Argon. After the reaction was complete, water was added and the organic layer was extracted with $CH_2Cl_2$ and dried over anhydrous $Na_2SO_4$. After removal the solvent under reduced pressure, the residue was purified by column chromatography with $CH_2Cl_2$-Ethylacetate as eluent to give compound L-03 as a dark yellow solid (0.89 mmol, 65%). Anal. $C_{30}H_{22}BrN_5S_3$: Calcd: C, 57.32; H, 3.53; N, 11.14; Found: C, 57.53; H, 3.49; N, 11.20. MS (ESIMS): m/z: 629.1.

Preparation of Compound L-04: To a solution of compound L-03 in dry THF, n-BuLi (1.3 mmol, 1.6 M in hexane) was added at −78° C. under nitrogen. The mixture was stirred at −78° C. for 2 hrs and DMF (1.3 mmol) was added. After 1 h, the mixture was poured into aqueous HCl (4.5% 100 mL) and stirred at 0° C. for 1 h. The organic layer was extracted with $CH_2Cl_2$ and dried over $Na_2SO_4$. After removal of the solvent under reduced pressure, the residue was purified by column chromatography with $CH_2Cl_2$-Ethylacetate as eluent to give compound L-04 as a red solid (80% yield): Anal. $C_{31}H_{23}N_5OS_3$: Calcd: C, 64.45; H, 4.01; N, 12.12; Found: C, 64.61; H, 4.11; N, 12.03. MS (ESIMS): m/z: 577.2.

Preparation of dye C-1: To a mixture of L-04 (1.0 mmol), 2-cyanuric acid (1.0 mmol) and ammonium acetate (2.6 mmol) in acetonitrile (10 mL) was added 10 mL of glacial acetic and the mixture was stirred for 3 hr under Ar. After evaporation of the solvent, the crude solid was dissolved into $CH_2Cl_2$ and washed with water. The organic layer was dried over $Na_2SO_4$. After removal the solvent under reduced pressure, the residue was purified by recrystallization in acetonitrile to give dye C-1 as a red solid (85% yield). Anal. $C_{34}H_{24}N_6O_2S_3$: Calcd: C, 63.33; H, 3.75; N, 13.03; Found: C, 63.51; H, 3.81; N, 12.91. MS (ESIMS): m/z: 644.2.

EXAMPLE 2
Synthesis Process for C-2
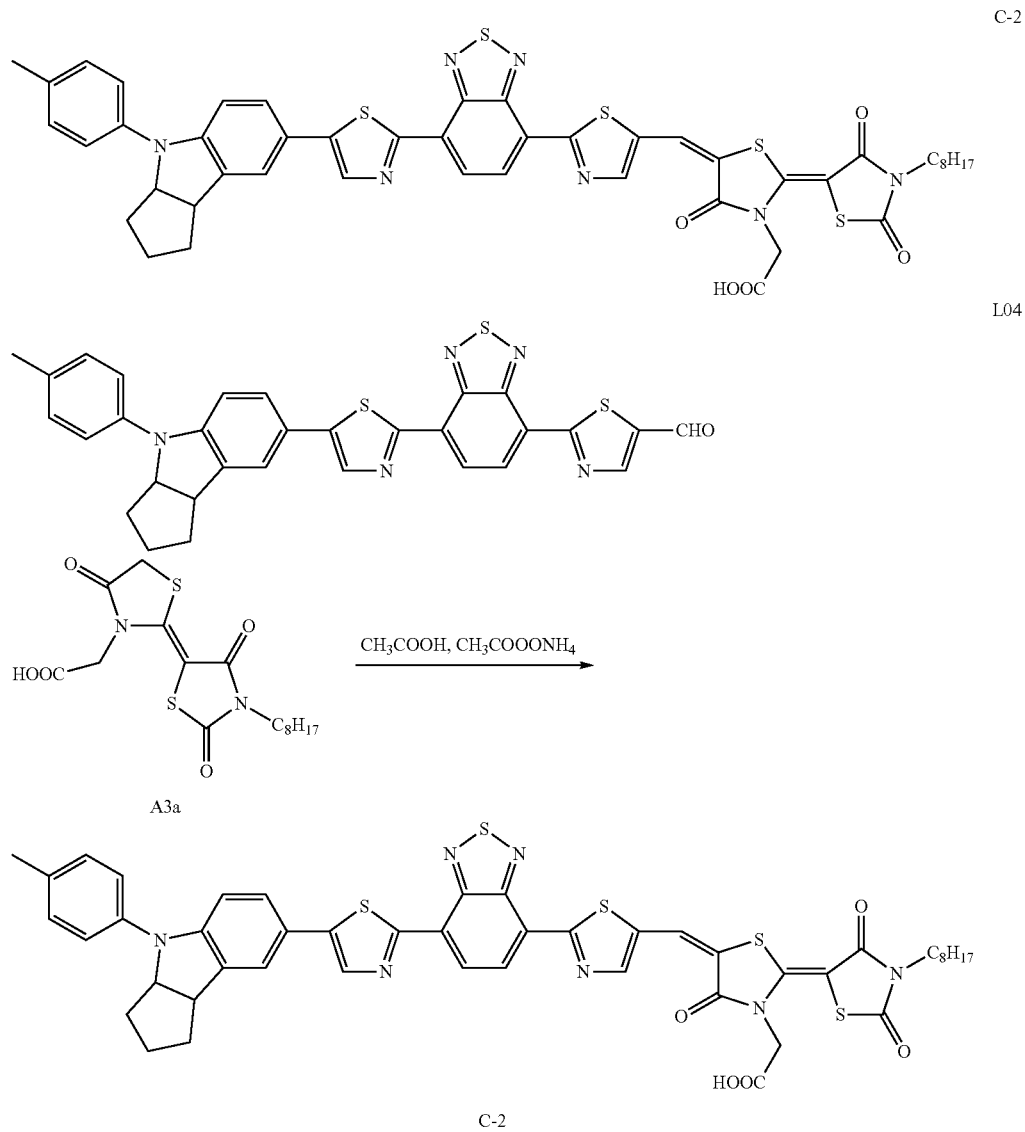
Preparation of Compound L-04: Compound L-04 was prepared as in Example 1 above.
Preparation of Compound A3a: This compound was prepared by an analogous procedure to that described in Shinji Higashijima, Hidetoshi Miura, Tomoki Fujita, Yasuhiro Kubota, Kazumasa Funabiki, Tsukasa Yoshidac, Masaki Matsui, *Tetrahedron* 67 (2011) 6289, as illustrated below.

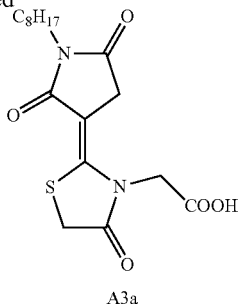

A3a

Ref. Tetrahedron 67 (2011) 6289

Synthesis of A3a-1: To an ethanol solution (24 ml) of double rhodanine A3a-2 (6.10 mmol) and 35% hydrogen peroxide (61.0 mmol) was added thionyl chloride (30.5 mmol) at 50° C. The mixture was stirred for 1 h. After cooling, water (200 ml) was added to the mixture. The product was extracted with chloroform (200 ml). The organic layer was dried over anhydrous sodium sulfate. After evaporating the extract in vacuo, the crude product was purified by column chromatography (SiO$_2$, CHCl$_3$) to give A3a-1 (46%) as a pale yellow solid: Anal. C$_{19}$H$_{28}$N$_2$O$_5$S: Calcd: C, 57.55; H, 7.12; N, 7.07; Found: C, 57.67; H, 7.19; N, 6.95. MS (ESIMS): m/z: 396.1.

Synthesis of A3a: To an acetic acid solution (1 ml) of A3a-1 (0.359 mmol) was added concd hydrochloric acid (0.5 ml). The mixture was refluxed for 3 h. After cooling, water (50 ml) was added. The product was extracted with chloroform (50 ml×2). The combined organic layer was dried over anhydrous sodium sulfate. After evaporating the extract under reduced pressure, the crude product was washed with hexane (30 ml) to afford A3a (34%) as a yellow solid. Anal. C$_{17}$H$_{24}$N$_2$O$_5$S: Calcd : C, 55.42; H, 6.57; N, 7.60; Found: 55.35; H, 6.62; N, 7.68, MS (ESIMS): m/z: 368.1.

Preparation of dye C-2: A mixture of compound L-04 (1.81 mmol), 3-ethyl-5-(3-carboxymethyl-4-oxo-thiazolidin-2-ylidene)rhodanine (A3a) (1.79 mmol), ammonium acetate (0.78 mmol) in acetic acid (10 ml) was heated at 120° C. for 3 h. After completed the reaction, it was allowed to cool to room temperature. A dark red solid collected by filtration and washed with distilled water (80 ml), diethyl ether (50 ml), methanol (30 ml) and purification of column chromatography to give the dye C-2 (40%): Anal. C$_{47}$H$_{43}$N$_7$O$_5$S$_5$: Calcd: C, 59.66; H, 4.58; N, 10.36; Found: C, 59.77; H, 4.63; N, 10.26. MS (ESIMS): m/z: 945.1.

EXAMPLE 3

Synthesis Process for C-4

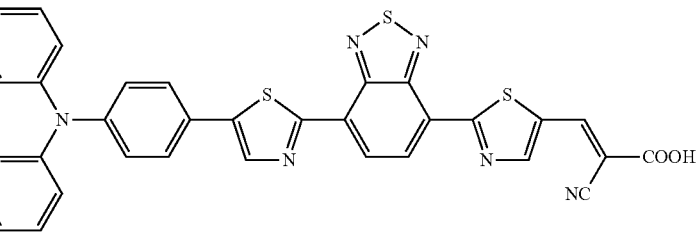

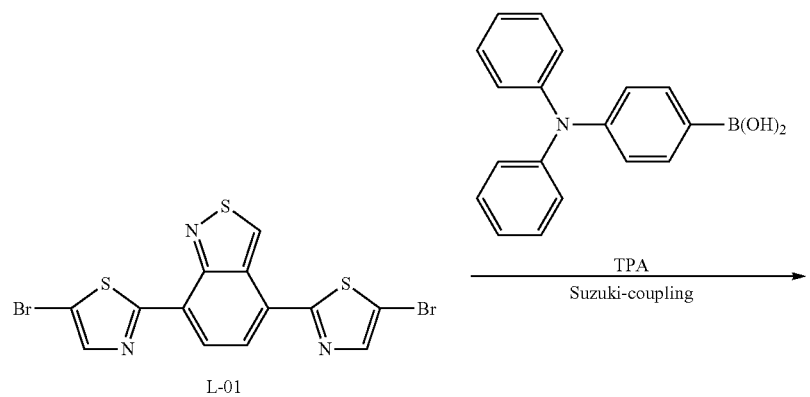

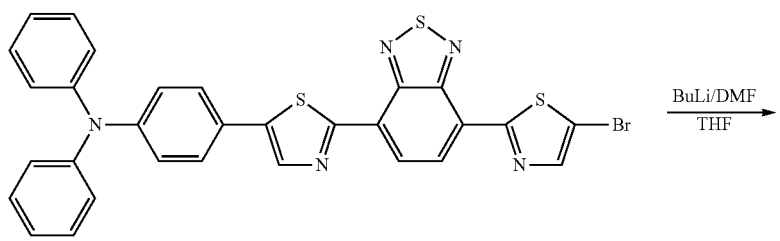

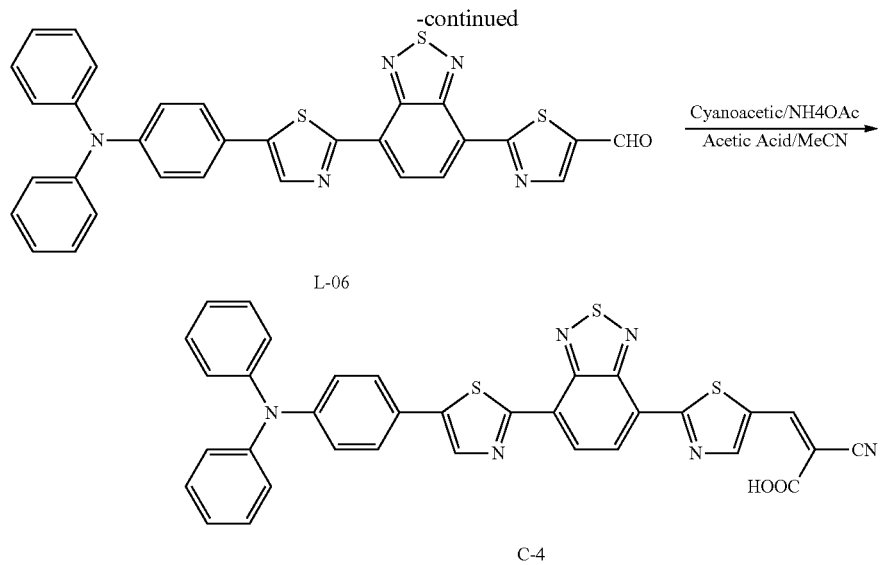

L-06

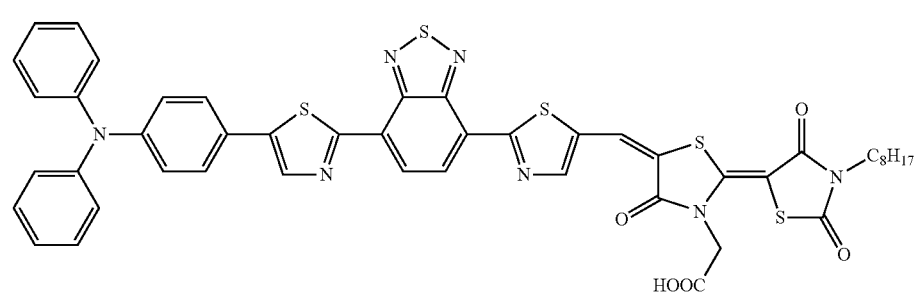

C-4

Preparation of Compound L-01: Compound L-01 was prepared as in Example 1 above.

Preparation of TPA-boronic acid: TPA-boronic Acid is commercially available (e.g. Supplier Name: Sigma-Aldrich, Catalog Publication Date: 29 Sep. 2011, 201802-67-7; 4-(Diphenylamino)-phenylboronic acid).

Preparation of compound L-05: A stirred mixture of L-01 (1.50 mmol), N,N-diphenyl-4-aminophenylboronic acid TPA (1.38 mmol), $Pd(PPh_3)_4$ (0.078 mmol), $K_2CO_3$ (2.0 mmol), THF (20 ml), $H_2O$ (2 ml) was refluxed for 10 h under Argon. After cooling, water was added and the product was extracted with $CH_2Cl_2$. The organic layer was collected, dried over anhydrous $Na_2SO4$ and evaporated under reduced pressure. The single substituted product was obtained by column chromatography ($CH_2Cl_2$/PE=1/10) on silica gel as a orange solid, L-05 (402 mg, 0.87 mmol, 63%). Yield: 61%. Yield: 55%. Anal. $C_{30}H_{18}BrN_5S_3$: Calcd: C, 57.69; H, 2.90; N, 11.21; Found: C, 57.75; H, 2.97; N, 11.12. MS (ESIMS): m/z: 625.0.

Preparation of compound L-06: To a solution of compound L-05 in dry THF, n-BuLi (1.3 mmol, 1.6 M in hexane) was added at −78° C. under nitrogen. The mixture was stirred at −78° C. for 2 hrs and DMF (1.3 mmol) was added. After 1 h, the mixture was poured into aqueous HCl (4.5% 100 mL) and stirred at 0° C. for 1 h. The organic layer was extracted with $CH_2Cl_2$ and dried over $Na_2SO_4$. After removal of the solvent under reduced pressure, the residue was purified by column chromatography with $CH_2Cl_2$-Ethylacetate as eluent to give compound L-06 as a red solid (70% yield): Anal. $C_{31}H_{19}N_5OS_3$: Calcd: C, 64.90; H, 3.34; N, 12.21; Found: C, 65.08; H, 3.41; N, 12.12. MS (ESIMS): m/z: 573.1.

Preparation of dye C-4: To a mixture of L-06 (1.0 mmol), 2-cyanuric acid (1.0 mmol) and ammonium acetate (2.6 mmol) in acetonitrile (10 mL) was added 10 mL of glacial acetic and the mixture was stirred for 3 hr under Ar. After evaporation of the solvent, the crude solid was dissolved into $CH_2Cl_2$ and washed with water. The organic layer was dried over $Na_2SO_4$. After removal the solvent under reduced pressure, the residue was purified by recrystallization in acetonitrile to give dye C-4 as a dark red solid (85% yield). Anal. $C_{34}H_{20}N_6O_2S_3$: Calcd: C, 63.73; H, 3.15; N, 13.12; Found: C, 63.66; H, 3.21; N, 13.22; MS (ESIMS): m/z: 640.1.

EXAMPLE 4

Synthesis of Dye C-5

C-5

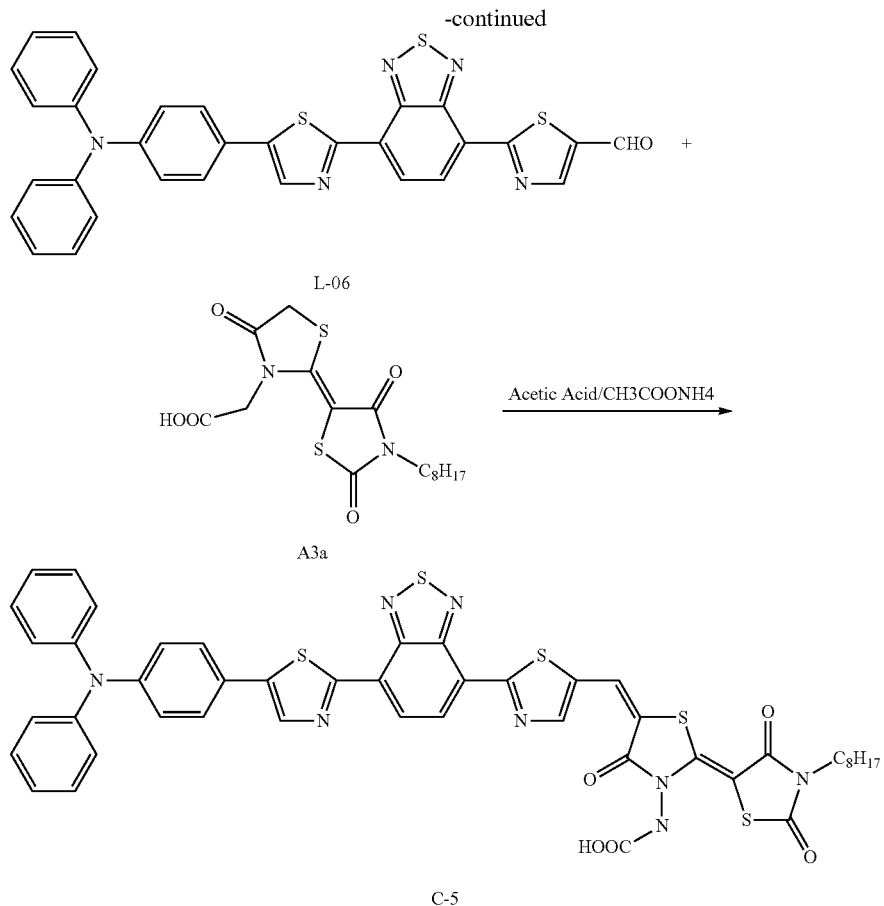

Preparation of Compound L-06: Compound L-06 was prepared as in Example 3, above.

Preparation of Compound A3a: Compound A3a was prepared as in Example 2, above.

Preparation of dye C-5: To a mixture of compound L-06 (1.81 mmol), 3-ethyl-5 -(3 -carboxymethyl-4-oxo-thiazolidin-2-ylidene)rhodanine (A3a) (1.79 mmol), ammonium acetate (0.78 mmol) in acetic acid (10 ml) was heated at 120° C. for 3 h. After completed the reaction, it was allowed to cool to room temperature. A dark red solid collected by filtration and washed with distilled water (80 ml), diethyl ether (50 ml), methanol (30 ml) and purification of column chromatography to give the dye C-5: Yield: 67%. Anal. $C_{47}H_{39}N_7O_5S_5$: Calcd: C, 59.91; H, 4.17; N, 10.41; Found: C, 59.82; H, 4.23 N, 10.35;. MS (ESIMS): m/z: 941.2.

Preparation of Sensitized Semiconductor Electrode:

Nanocrystalline $TiO_2$ films of about 12 μm were prepared by spreading a viscous dispersion of colloidal $TiO_2$ particles (Sloaronix) on a conducting glass support (Fluorine-doped $SnO_2$ over layer, transmission>85% in the visible, sheet resistance 7-8 ohms/square) with heating under air for 30 min at 500° C. The performance of the film as a sensitized photoanode was improved by further deposition of $TiO_2$ from aqueous $TiCl_4$ solution. A freshly prepared aqueous 0.2 M $TiCl_4$ solution was applied onto the electrode. After being left for 20 min at 70° C. in a closed chamber, the electrode was washed with distilled water. Immediately before being dipped into the dye solution, it was fired again for 30 min at 500° C. in air. After cooling under a continuous argon flow the glass sheet is immediately transferred to a $2\times10^{-4}$ M solution in 1:1 acetonitrile: tent-butanol of dye C-1 (example 1), this solution further containing 40 mM of deoxycholic acid as a co-adsorbent. The adsorption of photosensitizer from the dye solution is allowed to continue for 24 hours after that the glass sheet is withdrawn and washed briefly with absolute ethanol. The $TiO_2$ layer on the sheet assumed a dark color owing to the photosensitive coating.

Preparation of Solar Cell:

A solar cell (size: 0.25 $cm^2$) was fabricated using the above electrode and a counter electrode, which was a platinum electrode, obtained by vacuum-deposition of platinum on a conductive glass. The platinum layer had a thickness of 20nm. An electrolyte solution to be placed between the two electrodes was a redox pair of $I^-/I_3^-$ obtained using 0.5 M 4-tert-butylpyridine, 0.1 M LiI, 0.6M 1,2-dimethyl-3-propyl imidazolium iodide and 0.05 M $I_2$ as solutes and a liquid of acetonitrile.

Operation of Solar Cell:

A potentiostat was used for measuring short-circuit electric current, open circuit voltage and fill factor. Experiments are carried out with a high pressure Xenon lamp equipped with appropriate filters to simulate AM 1.5 solar radiation. The intensity of the light is 100 $mW/cm^2$. The fill factor defined as the maximum electric power output of the cell divided by the product of open circuit voltage and short circuit current.

The cell performance using dyes C-1, C-2, C-4 and C-5 under irradiation of air mass (AM) 1.5 using solar simulator light (100 $mW/cm^2$) are summarized in Table 1, below.

TABLE 1
| Sample | Jsc | Voc | FF | Efficiency |
|---|---|---|---|---|
| C-1 | 13.2 | 0.592 | 0.620 | 4.8 |
| C-2 | 13.3 | 0.553 | 0.641 | 4.7 |
| C-4 | 12.2 | 0.640 | 0.673 | 5.3 |
| C-5 | 11.3 | 0.594 | 0.619 | 4.2 |
What is claimed:
1. A photosensitizing dye of the structure C-1:
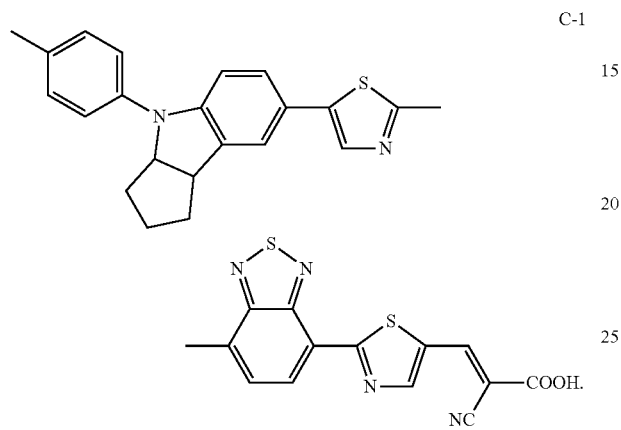
C-1
2. A photosensitizing dye of the structure C-2:
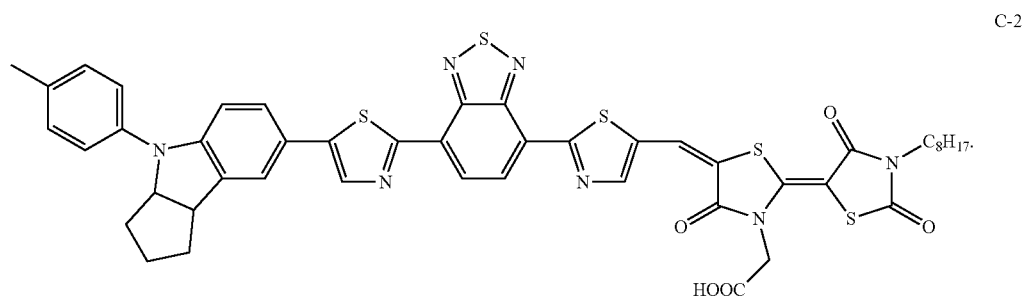
C-2
3. A photosensitizing dye of the structure C-3:
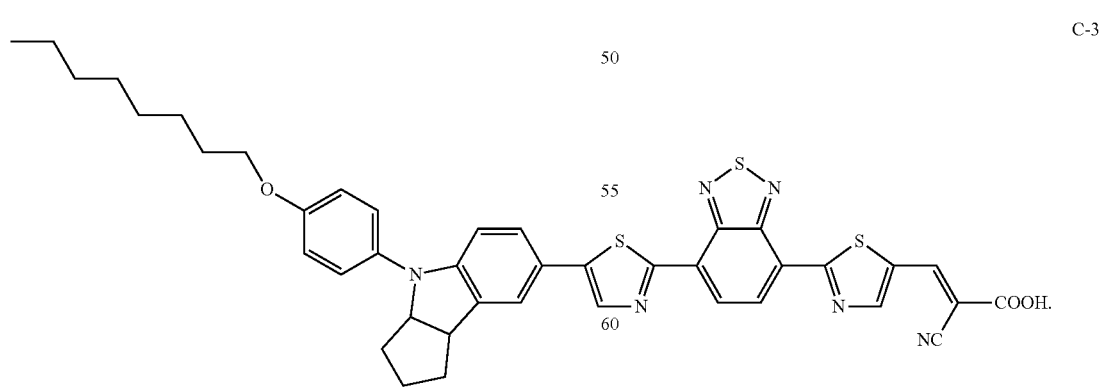 [SMILES: CCCCCCCCOc1ccc(N2c3ccc(-c4cnc(-c5ccc(-c6ncc(/C=C(\C#N)C(=O)O)s6)c6nsnc56)s4)cc3C3CCCC32)cc1]
C-3

4. A photosensitizing dye of the structure C-4:
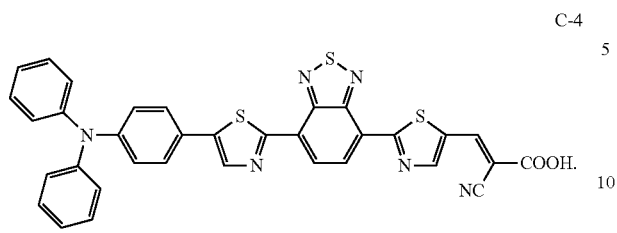
C-4
5. A photosensitizing dye of the structure C-5:
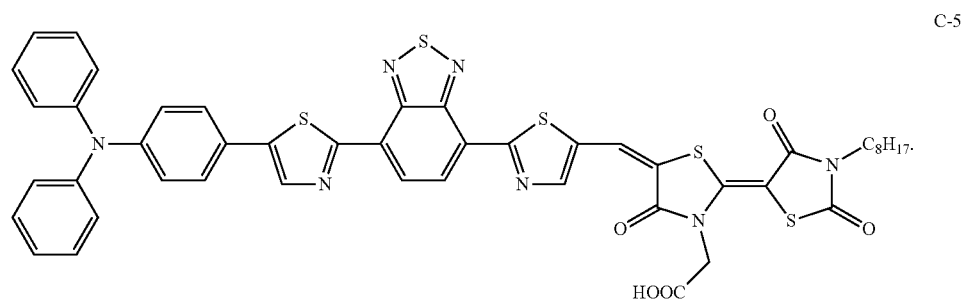
C-5
6. A photosensitizing dye of the structure C-6:
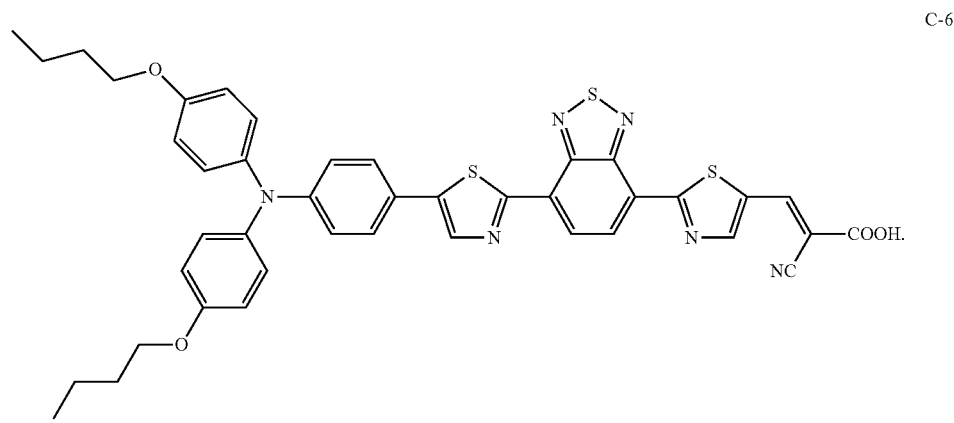 [SMILES: CCCCOc1ccc(N(c2ccc(OCCCC)cc2)c2ccc(-c3cnc(-c4ccc(-c5ncc(/C=C(\C#N)C(=O)O)s5)c5nsnc45)s3)cc2)cc1]
C-6
7. A photosensitizing dye of the structure C-7:
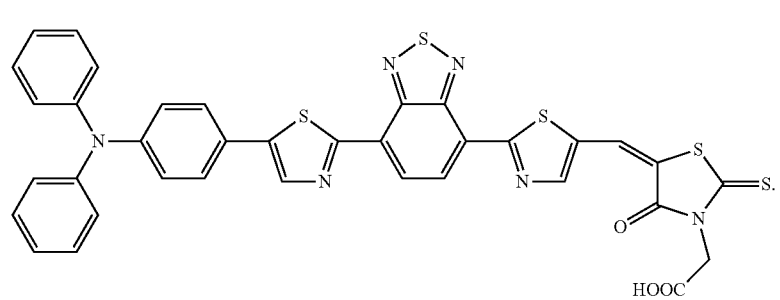
C-7
* * * * *